(12) United States Patent
Boger

(10) Patent No.: US 9,549,914 B2
(45) Date of Patent: Jan. 24, 2017

(54) TREATMENT OF HUMAN CYTOMEGALOVIRUS BY MODULATING WNT

(71) Applicant: THE JOHNS HOPKINS UNIVERSITY, Baltimore, MD (US)

(72) Inventor: Ravit Boger, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/678,128

(22) Filed: Apr. 3, 2015

(65) Prior Publication Data

US 2015/0306066 A1    Oct. 29, 2015

Related U.S. Application Data

(60) Provisional application No. 61/974,598, filed on Apr. 3, 2014.

(51) Int. Cl.
     *A61K 31/35*      (2006.01)
     *A61K 31/352*      (2006.01)

(52) U.S. Cl.
     CPC .................................. *A61K 31/352* (2013.01)

(58) Field of Classification Search
     USPC .................................................. 514/456, 451
     See application file for complete search history.

(56) References Cited

U.S. PATENT DOCUMENTS

| | | | |
|---|---|---|---|
| 3,995,027 A * | 11/1976 | Gale | A61K 36/06 424/115 |
| 5,200,051 A | 4/1993 | Cozzette et al. | |
| 5,466,575 A | 11/1995 | Cozzette et al. | |
| 5,554,339 A | 9/1996 | Cozzette et al. | |
| 6,479,255 B1 | 11/2002 | Rubin et al. | |
| 6,861,234 B1 | 3/2005 | Simard et al. | |
| 6,913,746 B2 | 7/2005 | Wyss et al. | |
| 7,598,031 B2 | 10/2009 | Liew | |
| 8,067,173 B2 | 11/2011 | Liew | |
| 8,101,358 B2 | 1/2012 | Liew | |
| 8,110,358 B2 | 2/2012 | Liew | |
| 8,114,597 B2 | 2/2012 | Liew | |

(Continued)

FOREIGN PATENT DOCUMENTS

| | | | |
|---|---|---|---|
| EP | 294538 | * | 1/1988 |
| WO | 9005910 A1 | | 5/1990 |

(Continued)

OTHER PUBLICATIONS

Leow et al. "Natural Compounds as Antagonists of canonical Wnt/beta-Catenin Signaling," Current Chemical Biology, 2010, vol. 4, pp. 49-63.*

(Continued)

*Primary Examiner* — Shengjun Wang

(74) *Attorney, Agent, or Firm* — Johns Hopkins Technology Transfer

(57) ABSTRACT

The present invention relates to the field of virology. More specifically, the present invention provides methods and compositions useful for treating human cytomegalovirus using Wnt pathway modulators. In a specific embodiment, a method for treating human cytomegalovirus (HCMV) in a patient in need thereof comprises administering an effective amount of Wnt pathway modulator.

2 Claims, 7 Drawing Sheets

(56) References Cited

U.S. PATENT DOCUMENTS

| | | |
|---|---|---|
| 8,133,674 B2 | 3/2012 | Liew |
| 8,133,675 B2 | 3/2012 | Liew |
| 8,148,072 B2 | 4/2012 | Liew |
| 8,257,922 B2 | 9/2012 | Liew |

FOREIGN PATENT DOCUMENTS

| | | | |
|---|---|---|---|
| WO | 9114004 A1 | | 9/1991 |
| WO | 9816641 A1 | | 4/1998 |
| WO | 9818810 A1 | | 5/1998 |
| WO | 9854325 A1 | | 12/1998 |
| WO | 0014262 A2 | | 3/2000 |
| WO | 0170776 A2 | | 9/2001 |
| WO | 0175092 A2 | | 10/2001 |
| WO | 0182963 A2 | | 11/2001 |
| WO | 02080952 A2 | | 10/2002 |
| WO | 03000682 A1 | | 1/2003 |
| WO | 04000164 A2 | | 12/2003 |
| WO | 2004004658 A2 | | 1/2004 |
| WO | 2004080478 A1 | | 9/2004 |
| WO | 2005015207 A2 | | 2/2005 |
| WO | 2005026329 A2 | | 3/2005 |
| WO | 2005040391 A1 | | 5/2005 |
| WO | 2006073458 A2 | | 7/2006 |
| WO | 2006078278 A2 | | 7/2006 |
| WO | 2006088490 A2 | | 8/2006 |
| WO | 2006093526 A2 | | 9/2006 |
| WO | 2006112872 A2 | | 10/2006 |
| WO | 2007146968 A2 | | 12/2007 |
| WO | 2008073160 A2 | | 6/2008 |
| WO | 2008116468 A2 | | 10/2008 |
| WO | 2008139457 A2 | | 11/2008 |
| WO | 2008156655 A2 | | 12/2008 |
| WO | 2009003492 A1 | | 1/2009 |
| WO | 2009039854 A2 | | 4/2009 |
| WO | 2009045443 A2 | | 4/2009 |
| WO | 2009106073 A2 | | 9/2009 |
| WO | WO 2009/155379 | * | 12/2009 |
| WO | 2010037397 A1 | | 4/2010 |
| WO | 2010132047 A1 | | 11/2010 |
| WO | 2011072875 A1 | | 6/2011 |
| WO | 2011113953 A2 | | 9/2011 |
| WO | 2012019104 A1 | | 2/2012 |
| WO | 2012055408 A1 | | 5/2012 |
| WO | 2012100248 A1 | | 7/2012 |

OTHER PUBLICATIONS

Kapoor et al. "Wnt Modulating agents inhibit human cytomegalovirus replication," Antimicroboal Agents and Chemotherapy, Jun. 2013, vol. 57, No. 6, pp. 2761-2767.*

Dundarov et al. English Translation of EP0294538A, 1988.*

Kaiser, C. et al (1987). Inhibition by monensin of human cytomegalovirus DNA replication. Arch Virol. vol. 94, Issue 3-4:229-45.

Angelova, M. et al. (2012). Human Cytomegalovirus Infection Dysregulates the Canonical Wnt/β-catenin Signaling Pathway. PLoS Pathog. Oct. 8 (10): e1002959.

Lu, D. et al (2011). Salinomycin inhibits Wnt signaling and selectively induces apoptosis in chronic lymphocytic leukemia cells. Proc Natl Acad Sci USA. vol. 108, Issue 32:13253-7.

Steininger, C. 2007. Novel therapies for cytomegalovirus disease. Recent Pat Antiinfect.Drug Discov. 2:53-72.

D'Aiuto, L. et al. 2012. Human induced pluripotent stem cell-derived models to investigate human cytomegalovirus infection in neural cells. PLoS.One. 7:e49700.

Lu, D. et al. 2011. Inhibition of Wnt signaling and cancer stem cells. Oncotarget. 2:587.

Cheeran, M. et al. 2009. Neuropathogenesis of congenital cytomegalovirus infection: disease mechanisms and prospects for intervention. Clin.Microbiol.Rev. 22:99-126.

Hayward, S. et al. 2006. Notch and Wnt signaling: mimicry and manipulation by gamma herpesviruses. Sci.STKE. 2006:re4.

He, R. et al. 2011. Recombinant Luciferase-Expressing Human Cytomegalovirus (CMV) for evaluation of CMV inhibitors. Virol.J. 8:40.

He, R. et al. 2012. Artemisinin-derived dimer diphenyl phosphate is an irreversible inhibitor of human cytomegalovirus replication. Antimicrob.Agents Chemother. 56:3508-3515.

He, R., et al. 2011. An artemisinin-derived dimer has highly potent anti-cytomegalovirus (CMV) and anti-cancer activities. PLoS.One. 6:e24334.

Fuchs, D. et al. 2009. Salinomycin induces apoptosis and overcomes apoptosis resistance in human cancer cells. Biochem. Biophys.Res.Commun. 390:743-749.

Ketola, K. et al. 2010. Monensin is a potent inducer of oxidative stress and inhibitor of androgen signaling leading to apoptosis in prostate cancer cells. Mol.Cancer Ther. 9:3175-3185.

Van Amerongen, R. et al. 2009. Towards an integrated view of Wnt signaling in development. Development 136:3205-3214.

Najdi, R. et al. 2011 Wnt signaling and colon carcinogenesis: beyond APC. J.Carcinog. 10:5.

Kohn, A. et al. 2005. Wnt and calcium signaling: beta-catenin-independent pathways. Cell Calcium 38:439-446.

Ketola, K. et al. 2012. Salinomycin inhibits prostate cancer growth and migration via induction of oxidative stress. Br. J.Cancer 106:99-106.

Reya, T. et al. 2005. Wnt signalling in stem cells and cancer. Nature 434:843-850.

Clevers, H. 2006. Wnt/beta-catenin signaling in development and disease. Cell 127:469-480.

Barker, N. et al. 2000. Catenins, Wnt signaling and cancer. Bioessays 22:961-965.

Willert, K. et al. 2006. Wnt signaling: is the party in the nucleus? Genes Dev. 20:1394-1404.

Johnson, D. et al. 1982. Monensin inhibits the processing of herpes simplex virus glycoproteins, their transport to the cell surface, and the egress of virions from infected cells. J.Virol. 43:1102-1112.

Bongers, G. et al. 2010. The cytomegalovirus-encoded chemokine receptor US28 promotes intestinal neoplasia in transgenic mice. J.Clin.Invest 120:3969-3978.

Lopez-Iglesias, C. et al. 1988. Effects of tunicamycin and monensin on the distribution of highly phosphorylated proteins in cells infected with herpes simplex virus type 1. J.Ultrastruct.Mol.Struct. Res. 101:173-184.

* cited by examiner

TREATMENT OF HUMAN CYTOMEGALOVIRUS BY MODULATING WNT

CROSS-REFERENCE TO RELATED APPLICATIONS

This application claims priority to U.S. Provisional Patent Application Ser. No. 61/974,598, filed Apr. 3, 2014, which is incorporated herein by reference in its entirety.

FIELD OF THE INVENTION

The present invention relates to the field of virology. More specifically, the present invention provides methods and compositions useful for treating human cytomegalovirus using Wnt pathway modulators.

BACKGROUND OF THE INVENTION

Infection with Human Cytomegalovirus (HCMV) continues to be a major threat for pregnant women, the immunocompromised population including patients with HIV-AIDS (1-3). Because of the limited agents available for HCMV therapy, the side effects associated with anti-HCMV compounds (all viral DNA polymerase inhibitors), and the emergence of resistant viral mutants during therapy (4-6), there is a pressing need to develop anti-HCMV compounds with novel mechanisms of action. Understanding the complex and evolving interaction of HCMV with the cellular machinery may lead to the development of novel anti-HCMV inhibitors.

SUMMARY OF THE INVENTION

The present invention is based, at least in part, on the discovery that modulation of the Wnt pathway results in human cytomegalovirus (HCMV) inhibition. Infection with HCMV continues to be a threat for pregnant women and immunocompromised hosts. Although limited anti-HCMV therapies are available, development of new agents is highly desired. Compounds that modulate virus-cell interaction can inhibit HCMV replication. The Wnt signaling pathway plays a critical role in embryonic and cancer stem cell development and is targeted by γ-herpesviruses, Epstein-Barr virus (EBV) and Kaposi's sarcoma-associated herpes virus (KSHV). HCMV infects stem cells during embryogenesis, including neural progenitor cells, and may target the Wnt pathway. To investigate the role of Wnt in HCMV replication in vitro, the present inventors tested monensin, nigericin and salinomycin, compounds reported to inhibit cancer stem cell growth by modulating the Wnt pathway. These compounds inhibited the replication of HCMV Towne and a ganciclovir-resistant clinical isolate. Although HCMV inhibition occurred prior to DNA replication, the inhibitory effect persisted throughout the full replication cycle. While IE1 protein expression was unchanged, there was significant inhibition of IE2, UL44 and pp65 proteins. HCMV infection resulted in significant and sustained decrease in expression of phosphorylated and total lipoprotein receptor related protein 6 (pWnt, Wnt), Wnt 5a/b, β-catenin, and modest decrease in Dvl2/3, while levels of the negative regulator Axin 1 were increased. Nigericin decreased the expression of pWnt, Wnt, Axin 1 and Wnt 5a/b in non-infected and HCMV-infected cells; changes in expression of these proteins, especially Wnt 5a/b and axin 1 were more significant in HCMV-infected cells compared to non-infected cells. These data illustrate the complex effects of HCMV on components of the canonical and non-canonical Wnt pathway, and the fine balance between Wnt and HCMV resulting in abrogation of HCMV replication.

Accordingly, in one aspect, the present invention provides methods and compositions useful for treating human cytomegalovirus. In a specific embodiment, a method for treating human cytomegalovirus (HCMV) in a patient in need thereof comprises administering an effective amount of Wnt pathway modulator. The present invention also provides methods for treating herpes simplex virus (HSV) in a patient in need thereof comprising administering an effective amount of Wnt pathway modulator.

In certain embodiments, the modulator is selected from the group consisting of a small molecule, an antibody, an aptamer, and an inhibitory nucleic acid molecule. In a specific embodiment, the modulator is a small molecule. In more specific embodiments, the modulator is monensin, nigericin, or salinomycin. In further embodiments, the modulator is a derivative of monensin, nigericin, or salinomycin. In a more specific embodiment, the modulator is narasin. Indeed, the modulator can be a general class of antibiotics that show activity as a Wnt pathway modulator. In other embodiments, the inhibitory nucleic acid molecule is an antisense oligonucleotide, a short interfering RNA (siRNA), or a short hairpin RNA (shRNA).

In one embodiment, a method for treating HCMV in a patient in need thereof comprises administering an effective amount of Wnt pathway modulator, wherein the modulator is monensin, nigericin, salinomycin or derivatives thereof. In another embodiment, a method for treating HSV in a patient in need thereof comprises administering an effective amount of Wnt pathway modulator, wherein the modulator is monensin, nigericin, salinomycin or derivatives thereof.

BRIEF DESCRIPTION OF THE FIGURES

FIG. 7A: Expression of Wnt5a/b, Axin1, β-catenin, and actin (control) in non-infected (Mock), and HSV1-infected HFFs (MOI=0.1) treated with monensin (0.1 µM), nigericin (0.1 µM), salinomycin (1 µM) and GCV (10 µM) was determined after 48 h. Representative data from three independent experiments is shown. FIG. 7B: Expression of Wnt5a/b, Axin1, β-catenin, and actin (control) in non-infected (Mock), and HSV1-infected HFFs (MOI=0.1) treated with monensin (0.2 µM), nigericin (0.2 µM) and salinomycin (2 µM) and GCV (10 µM) was determined after 48 h. Representative data from three independent experiments is shown.

DETAILED DESCRIPTION OF THE INVENTION

Figure 1:
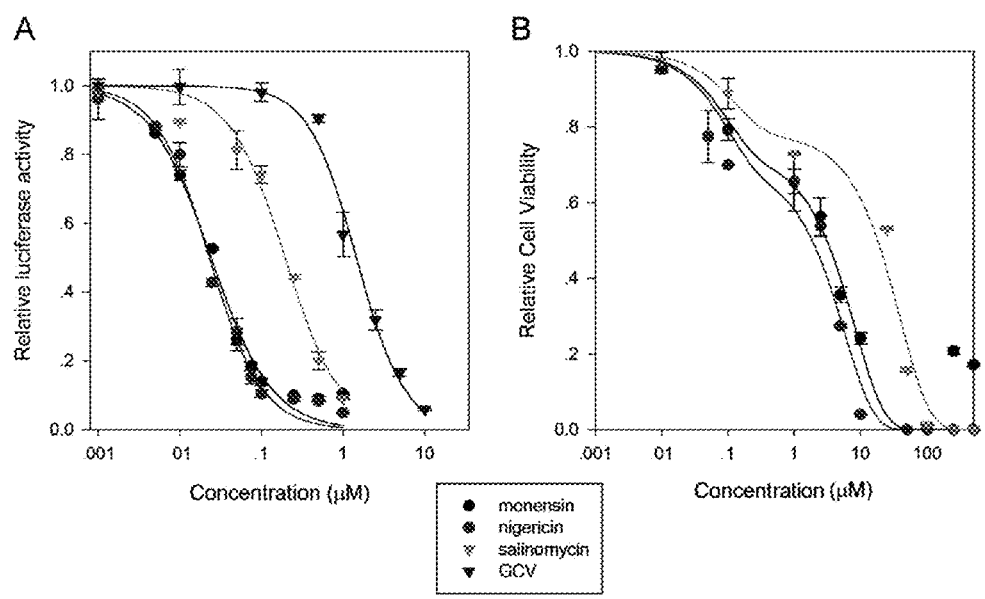
FIG. 1: Anti-HCMV activity and cellular toxicity of monensin, nigericin, salinomycin and GCV in HFFs. HFFs were infected with pp28-luc HCMV and treated with indicated concentrations of monensin, nigericin, salinomycin or GCV. Luciferase activity (A, left) and cytotoxicity (B, right) were measured at 72 hpi. Data represent mean values (±SD) of triplicate determinations from four independent experiments.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

HCMV persistently infects CD34+ hematopoietic progenitor and neural stem cells (7-10). Infection of neural stem cells reduces their capacity to differentiate into astrocytes, an observation that may explain, at least in part, the abnormalities in brain development observed in congenitally-infected children (9). The Wnt signaling pathway plays an important role in embryonic development, a time in which HCMV infects multiple cells and causes injury to major organs. Recent reports from cancer chemotherapy suggest that cure of cancers depends on targeting stem cells within the tumor environment which are usually resistant to available chemotherapeutic agents (11). Compounds that inhibit cancer stem cell growth via modulation of Wnt have recently been reported (11, 12). Because components of the Wnt signaling pathway are targeted by γ-herpesviruses, EBV and KSHV (13), we hypothesized that HCMV may also target the Wnt pathway and that modulation of Wnt by small molecules may affect HCMV replication. In this study the anti-HCMV activities of monensin, nigericin and salinomycin, compounds that were reported to inhibit Wnt signaling, were tested (12). These compounds demonstrated potent inhibition of HCMV replication, an effect associated with changes in the expression of proteins in the Wnt pathway, not previously known to be affected by HCMV.

I. DEFINITIONS

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the terms "Wnt modulator" and "Wnt pathway modulator" are used interchangeably herein and refer to an agent that modulates the Wnt pathway. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

As used herein, an "antagonist" is a type of modulator and the term refers to an agent that binds a target (e.g., a protein) and can inhibit a one or more functions of the target. For example, an antagonist of a protein can bind the protein and inhibit the binding of a natural or cognate ligand to the protein and/or inhibit signal transduction mediated through the protein.

An "agonist" is a type of modulator and refers to an agent that binds a target and can activate one or more functions of the target. For example, an agonist of a protein can bind the protein and activate the protein in the absence of its natural or cognate ligand.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against Wnt and used as Wnt modulators.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

"Optional" or "optionally" means that the subsequently described event or circumstance can or cannot occur, and that the description includes instances where the event or circumstance occurs and instances where it does not.

As used herein, a "subject" or "patient" means an individual and can include domesticated animals, (e.g., cats, dogs, etc.); livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. In particular, the term also includes mammals diagnosed with a Wnt pathway mediated disease, disorder or condition.

As used herein, the term "effective," means adequate to accomplish a desired, expected, or intended result. More particularly, a "therapeutically effective amount" as provided herein refers to an amount of a Wnt pathway modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a Wnt pathway modulator, necessary to provide the desired therapeutic effect, e.g., an amount that is effective to prevent, alleviate, or ameliorate symptoms of disease or prolong the survival of the subject being treated. In a particular embodiment, the disease or condition is infection with human cytomegalovirus. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In a specific embodiment, the disease or condition is infection with human cytomegalovirus.

The terms "Wnt-related disease, disorder or condition" or "Wnt-mediated disease, disorder or condition," and the like mean diseases, disorders or conditions associated with aberrant Wnt signaling. In a specific embodiment, the disease or condition is infection with human cytomegalovirus. In general, the term refers to any abnormal state that involves Wnt pathway activity. The abnormal state can be induced by environmental exposure or drug administration. Alternatively, the disease or disorder can be due to a genetic defect.

II. WNT PATHWAY MODULATORS

In certain embodiments, the Wnt Pathway modulator is selected from the group consisting of a small molecule, a polypeptide, a nucleic acid molecule, a peptidomimetic, or a combination thereof. In a specific embodiment, the agent can be a polypeptide. The polypeptide can, for example, comprise the extracellular domain of Wnt. The polypeptide can also comprise an antibody. In another embodiment, the agent can be a nucleic acid molecule. The nucleic acid molecule can, for example, be a Wnt inhibitory nucleic acid molecule. The Wnt inhibitory nucleic acid molecule can comprise a short interfering RNA (siRNA) molecule, a microRNA (miRNA) molecule, or an antisense molecule.

The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

In other embodiments, a Wnt pathway modulator is a small molecule. The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Examples of Wnt pathway modulators include monensin and its derivatives; nigericin and its derivatives; salinomycin and its derivatives, such as narasin; antisense oligonucleotides; short interfering RNA (siRNA); short hairpin RNA (shRNA); modifier of cell adhesion (MOCA) gene; small molecule tankyrase inhibitors such as XAV939; antibodies against Wnt1; antibodies against Wnt2; pan-Wnt inhibitors; antibodies targeting LRP5/6; antibodies targeting Fzds; targets of LRP5/6 phosphorylation; CK1 modulators; molecules which potentiate GSK3β activity; small molecules that increase levels of the scaffolding protein Axin; IWR-1; small molecule inhibitors of the Wnt pathway such as CWP232291; non-steroidal anti-inflammatory drugs (NSAIDs) such as aspirin, sulindac, and celecoxib; IWPs such as IWP-1 and IWP-2; acyltransferase Porcupine (Porcn) inhibitors; targets of CBP; targets of p300; targets of BCL9; targets of Pygopus; targets of Brg1; CBP/β-catenin antagonists such as ICG-001 and derivatives thereof; Traf2- and Nck-Interacting Kinase (TNIK) inhibitors; small molecule antagonists of the T cell factor (Tcf)/β-catenin protein complex such as PKF115-584, CGP049090, PKF222-815, PKF118-744, PKF118-310, ZTM000990, NPDDG39.024, and NPDDG1.024; gene targets of β-catenin-regulated transcription such as targets of c-Myc and cyclin D1; vitamins such as retinoids and 1α25,-dihydroxy-Vitamin D3; polyphenols such as quercetin, epigallocatechin-3-gallate (EGCG), curcumin, resveratrol, and differentiation-inducing factors (DIFs) such as DIF-1 and DIF-3; molecular targeted drugs such as PNU 74654, 2,4-diamino-quinazoline, ICG-001-related analogs, NSC668036, FJ9, 3289-8625, inhibitors of Wnt response (IWR), inhibitors of Wnt production (IWP), and XAV939; biologics such as antibodies targeting Wnt proteins, recombinant proteins such as WIF1 and SFRPs, and RNA interference targeting Wnt proteins; β-catenin/TCF interaction antagonists; transcriptional co-activator antagonists; targets of the PDZ domain of Dvl; Wnt monoclonal antibodies such as Soluble Wnt receptor (Fz 8 cysteine-rich domain fused to the human Fc domain) antibody (decoy receptor); Fz receptor antibody; Thiazolidinedione; AV65; and Artificial F-box protein.

Compound libraries may be screened for Wnt pathway modulators. A compound library is a mixture or collection of one or more putative modulators generated or obtained in any manner. Any type of molecule that is capable of interacting, binding or has affinity for Wnt may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative modulator or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation, A-Syntese-Biotech ApS, Akos-SC, G & J Research Chemicals Ltd., Life Chemicals, Interchim S. A., and Spectrum Info. Ltd.

III. FUNCTIONAL ASSAYS

The functional characteristics of Wnt pathway modulators can be tested in vitro and in vivo. Wnt pathway modulators (e.g., small molecules) may be tested by their ability to inhibit HCMV replication. Modulators can also be tested for the ability to interfere with Wnt's (or upstream/downstream pathway member's) ability to bind its natural ligands and Wnt pathway members, or to modulate certain biological processes.

Wnt (or pathway members) binding to ligands can be detected using Biacore® by immobilizing ligands to a solid support and detecting soluble Wnt binding thereto. Alternatively, Wnt can be immobilized, and the ligand binding thereto can be detected. Wnt/ligand binding can also be analyzed by ELISA (e.g., by detecting Wnt binding to immobilized ligands), or by fluorescence resonance energy transfer (FRET). To perform FRET, fluorophore-labeled Wnt binding to ligands in solution can be detected (see, for example, U.S. Pat. No. 5,631,169).

Wnt-ligand binding can also be detected via "liquid binding" methods, i.e., measuring affinity in liquid setting, instead of in an immobilized environment. Such methods are offered by Roche. Wnt-ligand binding can also be detected by coimmunoprecipitation (Lagace et al., 2006 J. Clin. Inv. 116(11):2995-3005). To examine Wnt-ligand binding in this manner, HepG2 cells are cultured in sterol-depleted medium for 18 hours. Purified Wnt is added to the medium in the presence of 0.1 mM chloroquine and the cells are incubated for one hour. Cells are lysed in mild detergent (1% digitonin w/vol). Wnt or a ligand is immunoprecipitated from cell lysates, separated by SDS-PAGE, and immunoblotted to detect the presence of coimmunoprecipitated the ligand or Wnt, respectively (Lagace et al., 2006 J. Clin. Inv. 116(11): 2995-3005). These assays may be conducted with a mutant form of Wnt that binds to the ligand with a higher avidity (Lagace et al., 2006, supra).

Wnt pathway modulators can be tested for the ability to increase or decrease ligand levels within the cells. For example, cells are cultured in sterol-depleted medium (DMEM supplemented with 100 U/ml penicillin, 100 µg/ml streptomycin sulfate, and 1 g/l glucose, 5% (vol/vol) newborn calf lipoprotein-deficient serum (NCLPDS), 10 µM sodium compactin, and 50 µM sodium mevalonate) for 18 hours to induce ligand expression. Purified Wnt (about 5 µg/ml) is added to the medium. Ligand levels in cells harvested at 0, 0.5, 1, 2, and 4 hours after addition of Wnt is determined (Lagace et al., 2006 J. Clin. Inv. 116(11):2995-3005). Ligand levels can be determined by flow cytometry, FRET, immunoblotting, or other means.

IV. METHODS OF USING WNT PATHWAY MODULATORS

The Wnt pathway modulators described herein have in vitro and in vivo diagnostic and therapeutic utilities. For example, these molecules can be administered to cells in culture, e.g., in vitro or in vivo, or in a subject, e.g., in vivo, to treat, prevent or diagnose a variety of Wnt-mediated diseases, disorders or conditions. In a specific embodiment, the disease, disorder or condition is infection with human cytomegalovirus. Wnt pathway modulators are particularly suitable for treating human patients suffering from "Wnt signaling-related disorders," meaning those diseases and conditions associated with aberrant Wnt pathway signaling. Aberrant upregulation of Wnt pathway signaling would be particularly amendable to treatment by the administration of antagonizing Wnt pathway modulators. Conversely, aberrant downregulation of Wnt pathway signaling would be particularly amendable to treatment by the administration of agonizing pathway modulators.

V. PHARMACEUTICAL COMPOSITIONS AND ADMINISTRATION

Accordingly, a pharmaceutical composition of the present invention may comprise an effective amount of a Wnt pathway modulator. As used herein, the term "effective," means adequate to accomplish a desired, expected, or intended result. More particularly, an "effective amount" or a "therapeutically effective amount" is used interchangeably and refers to an amount of a Wnt pathway modulator, perhaps in further combination with yet another therapeutic agent, necessary to provide the desired "treatment" (defined herein) or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat patients suffering from a Wnt-mediated disease, disorder or condition. As would be appreciated by one of ordinary skill in the art, the exact low dose amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which a Wnt pathway modulator is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a Wnt pathway modulator together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising a Wnt pathway modulator may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising a Wnt pathway modulator, optionally in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 µg-30 mg, about 0.01 µg-20 mg or about 0.01-10 mg per day to adults (at about 60 kg). In the case of other animals, the dose calculated for 60 kg may be administered as well.

Doses of a pharmaceutical composition of the present invention can optionally include 0.0001 µg to 1,000 mg/kg/administration, or 0.001 µg to 100.0 mg/kg/administration, from 0.01 µg to 10 mg/kg/administration, from 0.1 µg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions may further be combined with one or more additional therapeutic agents. In particular embodiments, the second therapeutic agent can be an antiviral. A combination therapy regimen may be additive, or it may produce synergistic results.

The compositions can be administered simultaneously or sequentially by the same or different routes of administration. The determination of the identity and amount of the pharmaceutical compositions for use in the methods of the present invention can be readily made by ordinarily skilled medical practitioners using standard techniques known in the art. In specific embodiments, a Wnt pathway modulator of the present invention can be administered in combination with an effective amount of another therapeutic agent, depending on the disease or condition being treated.

In various embodiments, the Wnt pathway modulator of the present invention in combination with an another therapeutic agent may be administered at about the same time, less than 1 minute apart, less than 2 minutes apart, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, the Wnt pathway modulator of the present invention in combination with another therapeutic agent is cyclically administered. Cycling therapy involves the administration of a first therapy (e.g., the Wnt pathway modulator) for a period of time, followed by the administration of a second therapy (e.g., another therapeutic agent) for a period of time, optionally, followed by the administration of perhaps a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Compounds.

Monensin, nigericin, salinomycin and ganciclovir (GCV), were purchased from Sigma Chemicals, (St. Louis, Mo.). A 10 mM stock solution of all compounds was stored in −80° C.

Viruses.

The pp28-luciferase HCMV Towne strain was constructed as previously described (14). This virus expresses luciferase under the control of the late CMV gene promoter, pp28. Luciferase expression is strongly activated 48-72 hours post infection (hpi). This recombinant virus provides a highly-sensitive and reproducible reporter system which correlates with the classic plaque reduction assay (14). A GCV-resistant HCMV strain was obtained from a patient with CMV disease. It has a UL97 mutation (H520Q) and an $EC_{50}$ of 7.6 µM for GCV. Human herpes virus strains were: luciferase HSV1-KOS/Dlux/oriS (15) and clinical isolates of HSV1 and HSV2. All clinical isolates were provided by the clinical virology laboratory with no identifiers that can link to a specific subject. The Johns Hopkins Office of Human Subject Research Institutional Review Board determined that this research qualified for an exemption.

Cell Culture, Virus Infection and Anti-Viral Assays.

Human Foreskin Fibroblasts (HFFs) passage 12-16 (ATCC, CRL-2088™) were grown in Dulbecco's Modified Eagle Medium (DMEM) containing 10% fetal bovine serum (FBS) (Gibco, Carlsbad, Calif.) in a 5% $CO_2$ incubator at 37° C. and used for infection with HCMV or HSV at multiplicity of infection of 1 PFU/cell (MOI=1) unless otherwise specified. Following 90 minute adsorption (60 min for HSV), media was removed and cells were washed with PBS. DMEM with 4% FBS containing compounds was added to each well. For HCMV, infected, treated HFFs were collected at 72 hpi and lysates were assayed for luciferase activity using a luciferase assay kit (Promega, Madison, Wis.) on GloMax®-Multi+ Detection System (Promega) according to manufacturer's instructions.

For HSV1-KOS/Dlux/oriS, a luciferase assay was performed 24 hpi. A yield reduction assay was performed with HSV1-KOS/Dlux/oriS. HFFs were infected and treated with the compounds. 48 hpi the supernatants from infected HFFs were collected and used for infection of fresh HFFs. Luciferase activity was measured after 16 hours. Plaque assays were performed with clinical isolates of HSV1 and HSV2. Vero cells were seeded at $3 \times 10^5$ cells per well in 12-well plates and were infected 24 hours later with HSV-1 or HSV-2 strains at 200 PFU/well. Following 60 minute adsorption, the virus was aspirated, and DMEM containing 0.5% carboxymethyl-cellulose, 4% fetal bovine serum (FBS), and compounds at indicated concentrations were added into triplicate wells. After incubation at 37° C. for 2 days, the overlay was removed and plaques were counted after crystal violet staining.

Real-Time PCR.

The quantitative CMV real-time PCR assay is based on detection of a 151 bp region from the highly conserved US17 gene (16). The limit of detection of the assay is 100 copies/mL (3.0 copies/reaction), and the measurable range is 2.4-8.0 $\log_{10}$ copies/mL. The PCR was performed using a total reaction volume of 50 µL, including TaqMan 2× Universal PCR Master Mix (Applied Biosystems, Foster City, Calif.), primers (300 nM final concentration), FAM-labeled probe (200 nM final concentration), $dH_2O$, and template (10 µl). Amplification was performed on a 7500 Real-Time PCR System (Applied Biosystems, Foster City, Calif.). PCR conditions were: 50° C. for 2 min, 95° C. for 10 min, 40 cycles of 95° C. for 15 s and 60° C. for 60 s. Quantification standards were prepared by cloning the US17 amplicon in the pCR®2.1-TOPO® plasmid vector (Invitrogen, Carlsbad, Calif.). Serial 10-fold dilutions of plasmid from 7.0 to 1.0 $\log_{10}$ copies/reaction were included with each assay and used to establish a standard curve. The slope and $R^2$ of the standard curve were −3.3±0.1 and >0.990, respectively. Assay controls included quantified CMV AD 169 DNA (Advanced Biotechnologies Inc.) and quantified Towne CMV at 3.0 and 5.0 $\log_{10}$ copies/mL. Quantitative CMV data were expressed as viral DNA copies per milliliter. The real-time PCR was used for quantification of HCMV replication in cell lysates at 48 hpi, virus DNA yield in supernatants at 96 hpi and for a reversibility assay (14, 16).

Cell Viability.

Cell viability was determined using a colorimetric MTT cell proliferation assay following manufacturer's instructions (Sigma-Aldrich, St. Louis, Mo.). HFFs were treated with varying concentrations of monensin, nigericin, and salinomycin and incubated at 37° C. for 3 days. After the addition of 20 µl/well of MTT (3-(4,5-Dimethyl-2-thiazolyl)-2,5-diphenyl-2H-tetrazolim bromide) (5 mg/ml in PBS), and shaking at 150 rpm for 5 minutes the plates were incubated at 37° C. for 3 hours. Conversion of yellow solution into dark blue formazan by mitochondrial dehydrogenases of living cells was quantified by measuring absorbance at 570 nM. Viable cells in culture medium containing vehicle alone (0.1% DMSO) were referred to as 100% cell viability. For each cell type used for virus infection and drug treatment, the MTT assay was performed at the same time points as the antiviral assay.

SDS-Polyacrylamide Gel Electrophoresis and Immunoblot Analysis.

Cell lysates were quantified for protein content using bicinchoninic acid (BCA) protein assay kit (Pierce Chemical, Rockford, Ill.). Equivalent amount of proteins were mixed with an equal volume of 2× sample buffer (125 mM Tris-HCL, pH 6.8, 4% SDS, 20% glycerol and 5% β-mercaptoethanol) and boiled at 100° C. for 10 min (except for Wnt and pWnt detection for which samples were not boiled). Denatured proteins were resolved in Tris-glycine polyacrylamide gels (10-12%) and transferred to polyvinylidine difluoride (PVDF) membranes (Bio-Rad Laboratories, Hercules, Calif.) by electroblotting. Membranes were incubated in blocking solution [5% non-fat dry milk and 0.1% Tween-20 in PBS (PBST)] for 1 hr, washed three times with PBST, and incubated with appropriately diluted primary antibodies at 4° C. overnight. Membranes were washed with PBST and incubated with horseradish peroxidase-conjugated secondary antibodies in PBST for 1 hr at room temperature. Following washing with PBST, protein bands were visualized by chemiluminescence using SuperSignal West Dura and Pico reagents (Pierce Chemical, Rockford, Ill.). The following antibodies were used for detection of CMV proteins: mouse anti-IE1 and IE2, (MAb810); mouse anti-beta-actin antibody (Millipore, Billerica, Mass.); mouse anti-UL44 (Santa Cruz biotechnology Santa Cruz, Calif.); mouse anti-pp65 (Vector laboratories, Burlingame, Calif.); horseradish peroxidase (HRP)-conjugated anti-rabbit IgG (Cell Signaling Technology, Beverly, Mass.); and HRP-conjugated anti-mouse IgG, (GE Healthcare, Waukesha, Wis.). The following antibodies were used for detection of proteins in the Wnt pathway: anti-Wnt5a/b, Wnt, phospho-Wnt, Dvl2, Dvl3 and axin1 (Cell Signaling), β-catenin (E-5) (Santa Cruz biotechnology).

Results

Example 1

Monensin, Nigericin and Salinomycin Inhibit HCMV Replication

Figure 2:
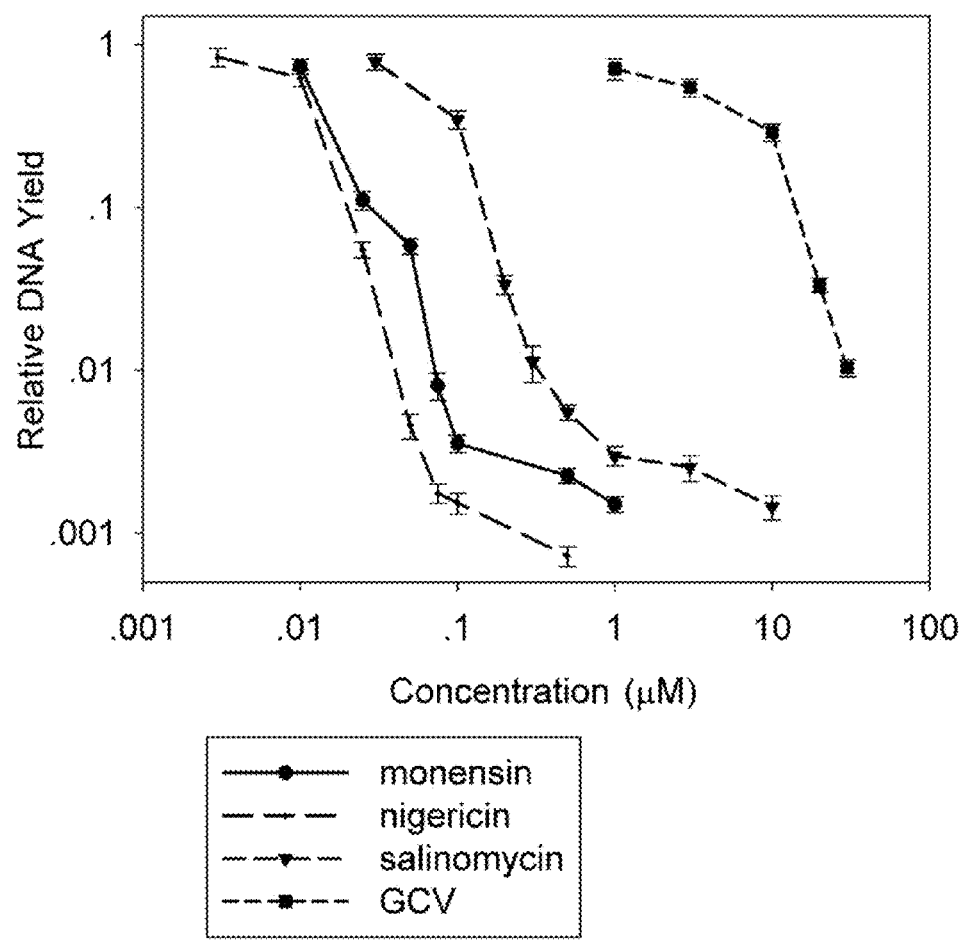
FIG. 2: Inhibition of a GCV-R HCMV strain by monensin, nigericin, salinomycin and GCV. HFFs cells were infected with a GCV-resistant HCMV and treated with monensin (0.01 μM-1 μM), nigericin (0.005 μM-0.5 μM), salinomycin (0.03 μM-10 μM) or GCV (1 μM-30 μM). Virus DNA yield was quantified by real-time PCR in supernatants of infected cells 96 hpi. Data represent mean values (±SD) of triplicate determinations from two independent experiments.

The anti-HCMV activities of monensin, nigericin and salinomycin were tested. At 1 µM >95% inhibition of HCMV replication (based on relative luciferase units) was achieved with all three compounds. A dose response curve was generated using concentrations ranging from 1 nM-1 µM (FIG. 1A). Although monensin and nigericin had a lower $EC_{50}$ (effective concentration resulting in 50% virus inhibition) than salinomycin, the selectivity index (SI) of the three compounds was similar and higher than 100 (Table 1). The slope of the dose response curve was also similar amongst the compounds and close to 1 (similar to the slope of GCV), suggesting an inhibitory effect via a possible shared target. The three compounds were toxic to colon carcinoma HCT116 and cervical cancer HeLa cells, but toxicity in HFFs was significantly lower (Table 1). The $CC_{50}$ (concentration resulting in 50% cell toxicity) in non-infected HFFs was 30-80 times higher than that measured in the tested cancer cells (FIG. 1B, Table 1). The three compounds were similarly effective in inhibiting a GCV-resistant HCMV strain (FIG. 2) based on virus DNA yield measured in supernatants of infected cells, suggesting an activity that is independent of the UL97 kinase.

TABLE 1

Anti-HCMV activity, cellular toxicity in HFFs and cancer cells, selectivity index (SI) and slope

| Compounds | $EC_{50}$ (µM) | $CC_{50}$ (µM) HFF | SI | slope | $CC_{50}$(µM) HeLa | $CC_{50}$(µM) HCT116 |
|---|---|---|---|---|---|---|
| Monensin | 0.02 ± 0.00 | 3.37 ± 0.52 | 138 ± 14 | 1.2 ± 0.11 | 0.07 ± 0.011 | 0.08 ± 0.02 |
| Nigericin | 0.02 ± 0.00 | 3.35 ± 0.77 | 139 ± 23 | 1.4 ± 0.16 | 0.04 ± 0.01 | 0.07 ± 0.01 |
| Salinomycin | 0.2 ± 0.01 | 28.4 ± 5.9 | 143 ± 18 | 1.4 ± 0.16 | 1.02 ± 0.08 | 1.17 ± 0.10 |
| GCV | 2.7 ± 0.1 | 247 ± 33.4 | 96 ± 14 | 1.3 ± 0.06 | >100 | >100 |

The $EC_{50}$, $CC_{50}$ and SI of monensin, nigericin and salinomycin against HCMV in different cell lines are shown. Data represent mean values (±SD) of triplicate determinations from at least three independent experiments.

Example 2

Figure 3:
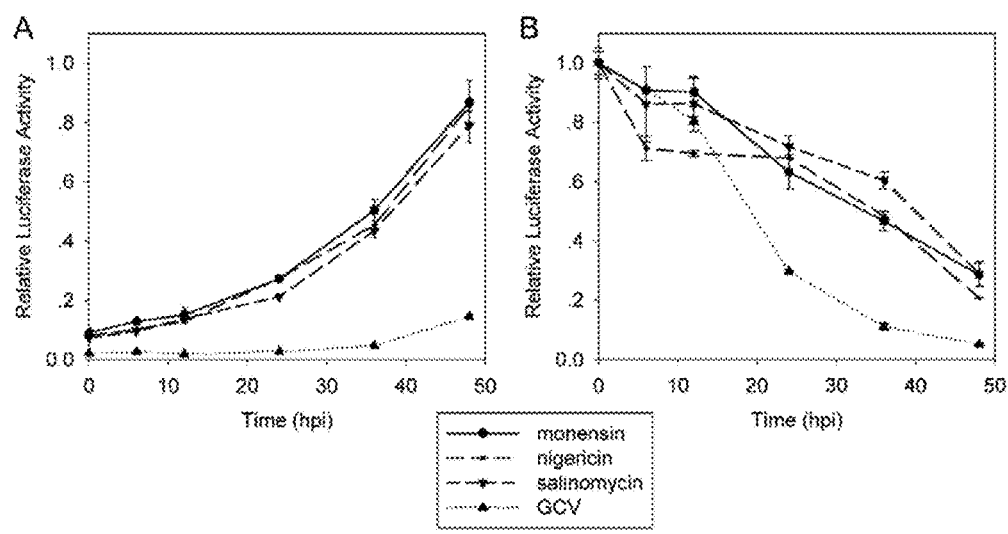
FIG. 3: Add on and removal of monensin, nigericin and salinomycin. In the add-on assay HFFs were infected with pp28-luc HCMV and compounds were added at 0, 6, 12, 24, and 48 hpi (Add on). The concentrations used were: 0.1 μM for monensin and nigericin, 1 μM for salinomycin and 10 μM for GCV. Luciferase activity was measured at 72 hpi. In the removal assay HFFs were infected with pp28-luciferase HCMV and treated with compounds immediately after virus adsorption. Compounds were removed at 0, 6, 12, 24 and 48 hpi (Removal). Luciferase activity was measured at 72 hpi. Data represent mean values (±SD) of triplicate determinations from three independent experiments.

Monensin, Nigericin and Salinomycin are Effective at Multiple Stages of HCMV Replication To determine the timing of HCMV inhibition an add-on and removal assay was performed. Compounds were added or removed at 0, 6, 12, 24 and 48 hpi and luciferase activity was measured at 72 hpi. The three compounds were similar to each other in both the add-on and removal assay. When compounds were added at or after 24 hours they were less effective against HCMV replication, suggesting HCMV inhibition occurred during the immediate early and early stages of HCMV replication. However, the removal assay revealed gradual decrease of virus replication by the three compounds (FIG. 3). Approximately 75% virus inhibition was achieved when compounds were removed at the 48 hr time point. This pattern of anti-HCMV activity is notably different from that of GCV and other HCMV inhibitors such as artemisinins (17).

Example 3

HCMV Inhibition is Largely Reversible by the Compounds

Figure 4:
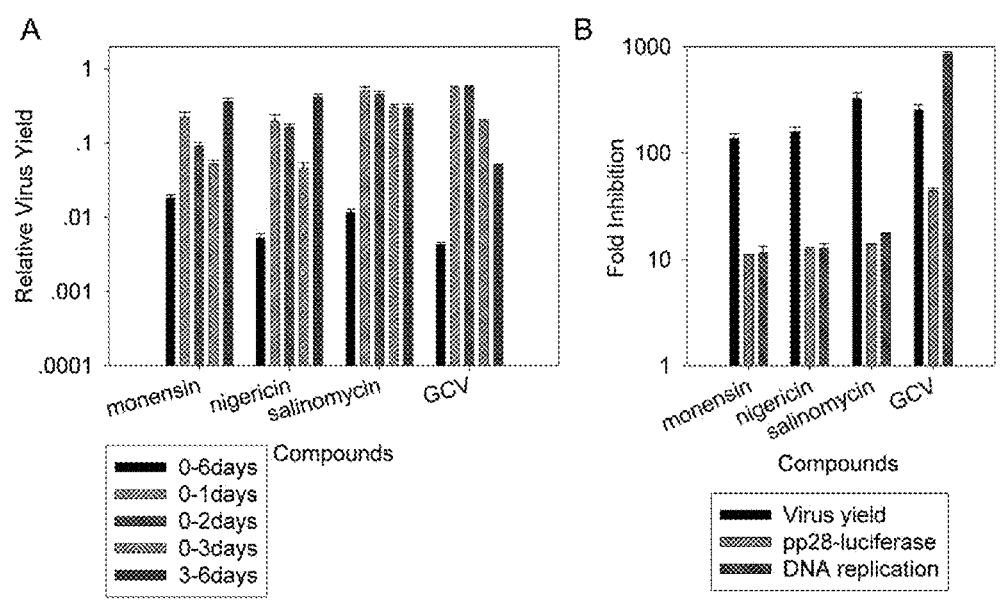
FIG. 4: Effects of monensin, nigericin, salinomycin and GCV on replication characteristics. A. Reversibility of HCMV replication: Compounds were present in HCMV-infected HFFs at the indicated intervals in days. Virus DNA was quantified by real-time PCR in supernatants at 6 days post infection. Data represent mean values (±SD) of triplicate determinations from two independent experiments. B. Inhibition of DNA replication, pp28 expression and virus DNA yield: DNA replication was quantified by real-time PCR in cells collected 48 hpi. Pp28-luciferase activity was measured in cell lysates collected at 72 hpi. Virus DNA yield was measured by real-time PCR in supernatants of infected cells collected at 96 hpi. The concentration of compounds was: 0.1 µM for monensin and nigericin, 1 µM for salinomycin and 10 µM for GCV. Data represent mean values (±SD) of triplicate determinations from two independent experiments.

To test whether HCMV inhibition by monensin, nigericin and salinomycin was reversible, infected HFFs were treated for 1, 2, or 3 days followed by removal of the media containing the compounds, and adding fresh media until 6 days post infection. HCMV DNA was quantified in supernatants of infected cells at day 6 post infection by real-time PCR. Similar to GCV, salinomycin was fully reversible when removed after 3 days (FIG. 4a). Monensin and nigericin showed weak irreversible inhibition of HCMV replication when present in infected cells longer than 48 hr.

Example 4

Inhibition of HCMV DNA Yield is More Efficient than Inhibition of Late Gene Expression and DNA Replication We recently reported that HCMV inhibitors may have varied effects on DNA replication and virus yield (based on real time PCR in supernatants of infected cells) (17). While the DNA polymerase inhibitor, GCV, inhibited virus yield and DNA replication at similar potency, the inhibition of virus yield by artemisinins was approximately 10-fold higher than the inhibition of DNA replication. The effects of monensin, nigericin and salinomycin on DNA replication, late gene expression and virus DNA yield were evaluated. Similar to artemisinins, the three compounds inhibited virus DNA yield at least 10-fold more than the inhibition of DNA replication (FIG. 4b), suggesting HCMV inhibition was not simply a result of direct targeting of the DNA replication machinery.

Example 5

Figure 5:
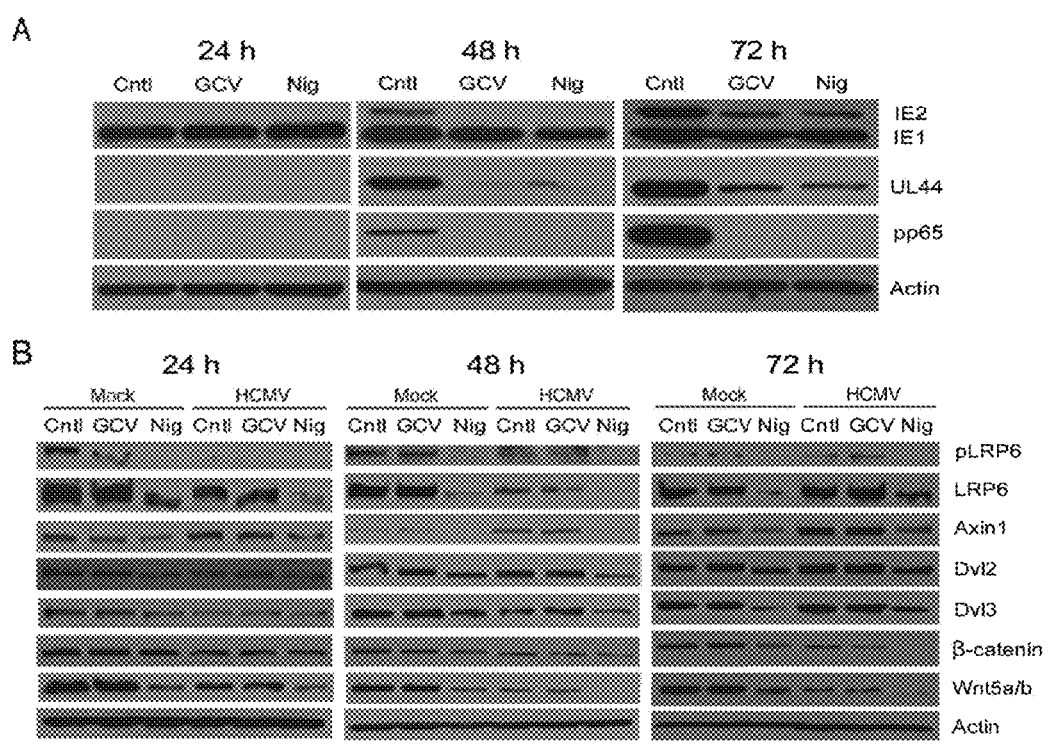
FIG. 5: Effect of Nigericin and GCV on expression of HCMV and Wnt/β-catenin signaling proteins. A. Expression of HCMV proteins in infected HFFs treated with nigericin (100 nM) and GCV (10 µM). Compounds were added after virus adsorption and cell lysates were collected for western blot at 24, 48 and 72 hpi. Control-no treatment. B. Expression of Wnt-signaling proteins was determined in non-infected (Mock), and HCMV-infected HFFs treated with nigericin (100 nM) and GCV (10 µM) at indicated time points. Representative data from three independent experiments are shown.

Inhibition of HCMV Protein Expression and Virus Progeny by Monensin, Nigericin and Salinomycin The effect of nigericin on HCMV gene expression was tested (FIG. 5a). There was no obvious inhibition of IE1 expression, but a major inhibition of IE2 and UL44 was observed at different time points (24, 48 and 72 hpi). There was also a significant inhibition in the expression of the late HCMV gene pp65. Determination of infectious virus released into the medium from infected HFFs treated with monensin and nigericin at 0.1 µM or salinomycin at 1 µM (yield reduction) revealed complete absence of plaques, suggesting the detection of DNA by real-time PCR from supernatants of infected-treated-cells represent non-infectious virus. These results further support our observations that HCMV inhibition by monensin, nigericin and salinomycin is likely a multi-staged process that is potentiated from early to late stage of virus replication.

Example 6

Figure 6:
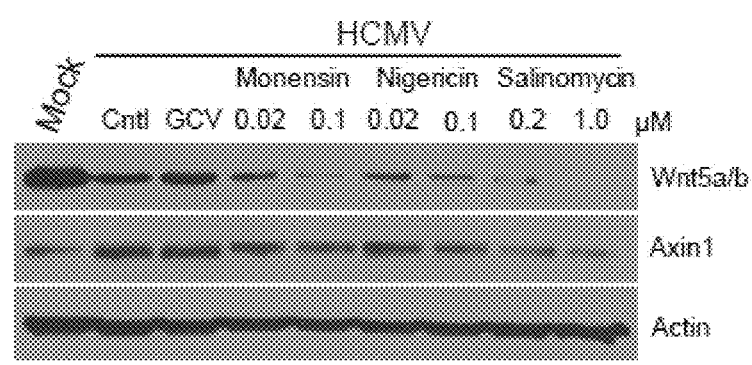
FIG. 6: Dose-dependent decrease in expression of Wnt5a/b and Axin1 by monensin, nigericin and salinomycin. Expression of Wnt5a/b, Axin1 and actin (control) in non-infected (Mock) and HCMV-infected HFFs (MOI=1) treated with GCV (10 µM), monensin (0.02, 0.1 µM), nigericin (0.02, 0.1 µM) and salinomycin (0.2, 1 µM) was determined after 72 h. Representative data from two independent experiments is shown.

Modulation of the Wnt Pathway by Monensin, Nigericin and Salinomycin in HCMV-Infected Cells is Associated with Inhibition of HCMV Replication The effect of nigericin and GCV on the expression of Wnt proteins (Wnt, phospho-Wnt, Wnt5a/b, Dvl2, Dvl3 and axin 1) was tested in non-infected and HCMV-infected HFFs (FIG. 5b). At 24, 48 and 72 hpi HCMV infection resulted in significant decrease in the expression of Wnt 5a/b and β-catenin, with no significant change in Dvl2 and Dvl3 expression between infected and non-infected cells. Phosphorylated and total lipoprotein receptor related protein 6 (pWnt, Wnt) levels were significantly reduced in HCMV-infected cells at 24 and 48 hpi. HCMV infection resulted in enhanced and sustained expression of the negative Wnt regulator, axin 1. At all time points treatment with nigericin resulted in decreased expression of pWnt, Wnt, axin 1 and Wnt 5a/b in non-infected and HCMV-infected cells. Treatment with nigericin also resulted in significant decrease in β-catenin levels, an effect that was increased as infection proceeded from 24 to 48 and 72 hpi. A correlation between HCMV inhibition and expression of Wnt 5a/b and axin 1 was observed with all three compounds (FIG. 6).

Example 7

Different Pattern of HSV1 and HSV2 Inhibition by Wnt Modulators

Figure 7:
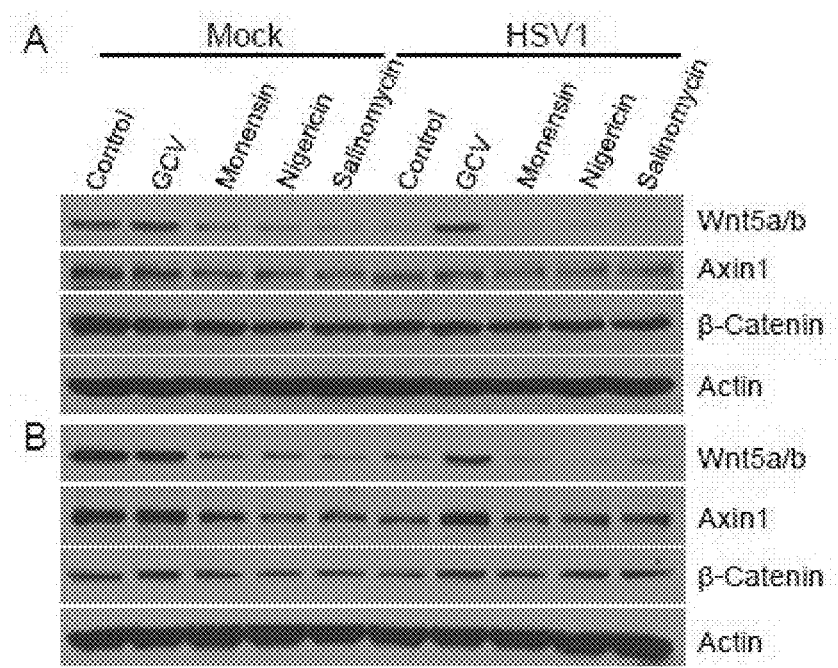
FIG. 7: Effect of monensin, nigericin and salinomycin on expression of Wnt/β-catenin signaling proteins in non-infected and HSV1-infected HFFs.

The activity of monensin, nigericin and salinomycin against HSV1 and HSV2 replication was tested. The compounds did not inhibit luciferase expression measured at 24 hpi with HSV1-KOS (Dlux/OriS), but plaque formation was strongly inhibited at 48 hpi. Since the luciferase in HSV1-KOS is regulated by an immediate early kinetics, these compounds did not inhibit HSV1 replication at an IE/E stage, while the inhibition of HCMV started at an IE stage. The supernatants of HFFs infected with HSV1-KOS (Dlux/OriS) and treated with the three compounds were harvested at 48 hpi and used for infection of fresh HFFs. Luciferase activity was measured after 16 hours in the newly infected HFFs and revealed the compounds were active against HSV1 replication (Table 2), suggesting inhibition occurred at a later stage of HSV1 replication. In addition, monensin, nigericin and salinomycin inhibited plaque formation of HSV1 and HSV2 in Vero cells (Table 2). The effect of monensin, nigericin and salinomycin on expression of components of Wnt in HSV1-infected HFFs was different from their effect in HCMV-infected and treated HFFs (FIG. 7). At 48 hpi with HSV1-KOS (Dlux/OriS) and treatment with concentrations resulting in full HCMV inhibition monensin, nigericin and salinomycin did not reduce the expression of β-catenin or axin 1, while inhibition of Wnt 5a/b was observed (FIG. 7A). A similar effect on Wnt protein expression was also observed at concentrations resulting in full inhibition of HSV1 (FIG. 7B). Taken altogether the mechanisms of HCMV and HSV inhibition by monensin, nigericin and alinomycin are likely distinct and may depend on pathways that are not fully shared between these viruses.

TABLE 2

Anti-HSV activity of monensin, nigericin and salinomycin

| Compounds (MW) | HSV1 | | HSV2 |
| --- | --- | --- | --- |
| | $EC_{50}$ (µM) Plaque Number (Vero) | $EC_{50}$ (µM) Yield Reduction (HFFs) | $EC_{50}$ (µM) Plaque Number (Vero) |
| Monensin | 1.6 ± 0.14 | 0.08 ± 0.0 | 0.34 ± 0.04 |
| Nigericin | 0.63 ± 0.00 | 0.08 ± 0.0 | 0.16 ± 0.05 |
| Salinomycin | 0.58 ± 0.07 | 0.6 ± 0.1 | 0.07 ± 0.03 |

The $EC_{50}$ of plaque number and yield reduction represents the average of triplicate measurements form two experiments.

DISCUSSION

The data presented show for the first time that HCMV infection of HFFs is associated with complex changes in the expression of multiple proteins of the Wnt pathway and that modulators of this pathway, monensin, nigericin and salinomycin are potent inhibitors of HCMV replication without causing toxicity to HFFs. These three compounds may share a similar mechanism of HCMV inhibition reflected by their slope, SI and antiviral assays. The add-on and removal assay suggests inhibition of HCMV replication occurs at several stages. Since the slope of the dose-response curve of the three compounds was close to 1 (Table 1), their effects may involve a viral protein that associates with a cellular target which is critical throughout the full replication cycle. Studies are ongoing to determine whether indeed a viral target is involved in the activity of these compounds. While the tested compounds did not affect IE1 expression at 24, 48 or 72 hpi, the early late gene, UL44, and IE2 were significantly decreased. The inhibitory effect was noted to augment itself as replication proceeded: DNA replication was inhibited at 48 hpi, pp65 gene expression was undetectable at 72 hpi, and a yield reduction assay revealed complete absence of plaques in infected HFFs treated with the three compounds. In contrast to the activation of the Wnt/β catenin by the oncogenic EBV and KSHV, HCMV infection resulted in inhibition of several components of the Wnt pathway, while axin 1 expression was enhanced at all tested time points. Moreover, HCMV inhibition with Wnt modulators was associated with significant and further downregulation of several components of both the canonical and non-canonical Wnt pathway. The expression of Wnt5a, which activates the β-catenin-independent pathway, but negatively regulates β-catenin-dependent activity (18) was significantly decreased throughout HCMV infection of HFFs and even more so after treatment with nigericin. Several anti-cancer agents (gleevec, roscovitine, rapamycin) were reported to inhibit HCMV replication, likely by interfering with one or more cell signaling pathways (19-21). The drawback of these agents is their toxicity to cancer cells as well as to non-cancerous primary HFFs. We have shown that the HCMV inhibitors, artemisinin dimers, have strong anti-cancer activities but are non-toxic to HFFs at concentrations that inhibit HCMV replication (22). A similar differential effect was reported with the Wnt modulators; while strongly inhibiting cancer cells, no toxic effects were found in the surrounding healthy cells (12, 23, 24). In agreement with these reports, we show here that cancer cells are exceedingly more sensitive to monensin, nigericin and salinomycin as compared to primary HFFs. Wnt signaling plays a crucial role in embryonic development and cancer, processes that are affected by HCMV. Originally, Wnt signals were classified into canonical (β-catenin-dependent) and non-canonical (β-catenin-independent). However, this pathway is now known to be more complex, Wnt action is context dependent and multiple intracellular cascades can be triggered, some a blend of canonical and non-canonical components (25, 26). The key characteristics of canonical signaling are the requirement for the LRP5/6 co-receptor to enable β-catenin accumulation and the involvement of LEF/TCF transcription factors. Wnt phosphorylation by glycogen synthase kinase-3 (GSK-3) and casein kinase-1γ (CK1) is crucial for activation of the canonical Wnt/β-catenin signaling (27). When a Wnt ligand binds to the (Frizzled) Fz receptor and its coreceptor Wnt, this complex together with the scaffolding protein Dishevelled (Dvl) results in Wnt phosphorylation, activation and recruitment of the axin complex to the receptors. These events lead to inhibition of axin-mediated β-catenin phosphorylation, stabilization of β-catenin, which accumulates and travels to the nucleus to activate Wnt target gene expression. The non-canonical Wnts avoid LRP co-receptors and β-catenin stabilization to activate intracellular kinases and regulate distinct β-catenin-independent pathways. These include the planar cell polarity (PCP) pathway and the Wnt/calcium pathway. The PCP pathway, mediated by Fz and Dvl, activates c-Jun-N-terminal kinase (JNK) and Rho-associated kinase (Rho-kinase). Non-canonical Wnts binding to Fz can also stimulate an increase in intracellular $Ca^{2+}$ levels, thereby activating calcium-sensitive proteins such as $Ca^{2+}$/calmodulin-dependent protein kinase II (CaM-KII) and protein kinase C (PKC) (28). Monensin, an ionophorous antibiotic isolated from *Streptomyces cinnamonensis* and used as an antibiotic in dairy cattle, was recently reported as a novel anti-neoplastic compound in prostate cancer cells (24, 29). Salinomycin, structurally similar to monensin, was identified as a breast cancer stem cell inhibitor in vitro and in vivo (30). It also reduced cancer and cancer stem cell growth in leukemias and uterine sarcoma cells (23). Nigericin and salinomycin inhibited Wnt signaling by blocking the phosphorylation of the Wnt coreceptor Wnt and inducing its degradation (12, 31-34). Monensin was reported in the past to block protein transport form the Golgi apparatus to the cell membrane and to inhibit HSV1, HSV2 and HCMV (35-38). Monensin treatment inhibited transport of progeny virus to the surface of infected cells while viral protein synthesis and DNA replication were not inhibited. The reduction of extra-cellular virus release was more significant for HSV2 than HSV1 (35). In the case of HCMV, monensin inhibited DNA replication and generation of virus progeny in HFFs and its activity was MOI dependent (37). These results correlate with our findings and suggest differences in activities of Wnt modulators between HSV- and HCMV-infected cells. Although the reports on monensin predated the discovery of Wnt and stem cell cancer, a correlation between the Wnt pathway and transport of proteins from Golgi in HCMV-infected cells remains to be studied. HCMV infection of HFFs resulted in decreased expression of multiple members (both canonical and non-canonical) of the Wnt pathway. Intriguingly, even further inhibition of Wnt signaling by monensin, nigericin or salinomycin resulted in HCMV inhibition, suggesting a very fine balance between virus and Wnt components that either maintains or abrogates lytic replication. A recent study reported on dysregulation of the canonical Wnt/β-catenin signaling pathway by HCMV. Infection induced degradation of β-catenin which resulted in a decrease in its transcriptional activity in response to Wnt ligand stimulation (39). HCMV also inhibited Wnt/β-catenin signaling in human extravillous cytotrophoblasts. Similarly, we found that HCMV infection resulted in decreased expression of total β-catenin. Another study showed that overexpression of HCMV-encoded US28 in intestinal epithelial cells inhibited GSK-3β function, promoted accumulation of β-catenin, and increased expression of Wnt target genes involved in the control of the cell proliferation (40). These studies and ours suggest the Wnt pathway is tightly regulated by HCMV. Virus replication mostly targets this pathway for inhibition of its components (with the exception of axin 1), and further inhibition of specific components results in virus inhibition. HCMV infection of the developing brain results in long-term neurological sequelae. How brain damage is induced by HCMV is not well-understood, but neural stem cells in the fetal brain appear to be an important cell type affected by the virus (41). The Wnt pathway may play an important role in neural stem cell development, differentiation and migration. In a murine CMV model, MCMV inhibited neuronal differentiation and decreased expression of Wnt-1 and neurogenin-1 (42).

We conclude that HCMV targets components of the Wnt pathway. While the γ herpesviruses KSHV and EBV activate the canonical Wnt/β-catenin pathway HCMV exerts different and mostly inhibitory effects on this pathway.

REFERENCES

1. Griffiths, P. D., D. A. Clark, and V. C. Emery. 2000. Betaherpesviruses in transplant recipients. J. Antimicrob. Chemother. 45 Suppl T3:29-34.
2. Kovacs, A., M. Schluchter, K. Easley, G. Demmler, W. Shearer, R. P. La, J. Pitt, E. Cooper, J. Goldfarb, D. Hodes, M. Kattan, and K. McIntosh. 1999. Cytomegalovirus infection and HIV-1 disease progression in infants born to HIV-1-infected women. Pediatric Pulmonary and Cardiovascular Complications of Vertically Transmitted HIV Infection Study Group. N. Engl. J. Med. 341:77-84.
3. Demmler, G. J. 1991. Infectious Diseases Society of America and Centers for Disease Control. Summary of a workshop on surveillance for congenital cytomegalovirus disease. Rev. Infect. Dis. 13:315-329.
4. Jabs, D. A., B. K. Martin, and M. S. Forman. 2010. Mortality associated with resistant cytomegalovirus among patients with cytomegalovirus retinitis and AIDS. Ophthalmology 117:128-132.
5. Steininger, C. 2007. Novel therapies for cytomegalovirus disease. Recent Pat Antiinfect. Drug Discov. 2:53-72.
6. Chou, S. W. 2001. Cytomegalovirus drug resistance and clinical implications. Transpl. Infect. Dis. 3 Suppl 2:20-24.
7. Goodrum, F. D., C. T. Jordan, K. High, and T. Shenk. 2002. Human cytomegalovirus gene expression during infection of primary hematopoietic progenitor cells: a model for latency. Proc. Natl. Acad. Sci. U.S.A 99:16255-16260.
8. Mendelson, M., S. Monard, P. Sissons, and J. Sinclair. 1996. Detection of endogenous human cytomegalovirus in CD34+ bone marrow progenitors. J. Gen. Virol. 77 (Pt 12):3099-3102.
9. Odeberg, J., N. Wolmer, S. Falci, M. Westgren, E. Sundtrom, A. Seiger, and C. Soderberg-Naucler. 2007. Late human cytomegalovirus (HCMV) proteins inhibit differentiation of human neural precursor cells into astrocytes. J. Neurosci. Res. 85:583-593.
10. D'Aiuto, L., M. R. Di, B. Heath, G. Raimondi, J. Milosevic, A. M. Watson, M. Bamne, W. T. Parks, L. Yang, B. Lin, T. Miki, J. D. Mich-Basso, R. Arav-Boger, E. Sibille, S. Sabunciyan, R. Yolken, and V. Nimgaonkar. 2012. Human induced pluripotent stem cell-derived models to investigate human cytomegalovirus infection in neural cells. PLoS. One. 7:e49700.
11. Lu, D. and D. A. Carson. 2011. Inhibition of Wnt signaling and cancer stem cells. Oncotarget. 2:587.
12. Lu, D., M. Y. Choi, J. Yu, J. E. Castro, T. J. Kipps, and D. A. Carson. 2011. Salinomycin inhibits Wnt signaling and selectively induces apoptosis in chronic lymphocytic leukemia cells. Proc. Natl. Acad. Sci. U.S.A 108:13253-13257.
13. Hayward, S. D., J. Liu, and M. Fujimuro. 2006. Notch and Wnt signaling: mimicry and manipulation by gamma herpesviruses. Sci. STKE. 2006:re4.
14. He, R., G. Sandford, G. S. Hayward, W. H. Burns, G. H. Posner, M. Forman, and R. Arav-Boger. 2011. Recombinant Luciferase-Expressing Human Cytomegalovirus (CMV) for evaluation of CMV inhibitors. Virol. J. 8:40.
15. Summers, B. C., T. P. Margolis, and D. A. Leib. 2001. Herpes simplex virus type 1 corneal infection results in periocular disease by zosteriform spread. J. Virol. 75:5069-5075.
16. Tanaka, Y., Y. Kanda, M. Kami, S. Mori, T. Hamaki, E. Kusumi, S. Miyakoshi, Y. Nannya, S. Chiba, Y. Arai, K. Mitani, H. Hirai, and Y. Mutou. 2002. Monitoring cytomegalovirus infection by antigenemia assay and two distinct plasma real-time PCR methods after hematopoietic stem cell transplantation. Bone Marrow Transplant. 30:315-319.
17. He, R., K. Park, H. Cai, A. Kapoor, M. Forman, B. Mott, G. H. Posner, and R. Arav-Boger. 2012. Artemisinin-derived dimer diphenyl phosphate is an irreversible inhibitor of human cytomegalovirus replication. Antimicrob. Agents Chemother. 56:3508-3515.
18. Ho, H. Y., M. W. Susman, J. B. Bikoff, Y. K. Ryu, A. M. Jonas, L. Hu, R. Kuruvilla, and M. E. Greenberg. 2012. Wnt5a-Ror-Dishevelled signaling constitutes a core developmental pathway that controls tissue morphogenesis. Proc. Natl. Acad. Sci. U.S.A 109:4044-4051.
19. Moorman, N. J. and T. Shenk. 2010. Rapamycin-resistant mTORC1 kinase activity is required for herpesvirus replication. J. Virol. 84:5260-5269.
20. Soroceanu, L., A. Akhavan, and C. S. Cobbs. 2008. Platelet-derived growth factor-alpha receptor activation is required for human cytomegalovirus infection. Nature 455:391-395.
21. Sanchez, V., A. K. McElroy, J. Yen, S. Tamrakar, C. L. Clark, R. A. Schwartz, and D. H. Spector. 2004. Cyclin-dependent kinase activity is required at early times for accurate processing and accumulation of the human cytomegalovirus UL122-123 and UL37 immediate-early transcripts and at later times for virus production. J. Virol. 78:11219-11232.
22. He, R., B. T. Mott, A. S. Rosenthal, D. T. Genna, G. H. Posner, and R. Arav-Boger. 2011. An artemisinin-derived dimer has highly potent anti-cytomegalovirus (CMV) and anti-cancer activities. PLoS. One. 6:e24334.
23. Fuchs, D., A. Heinold, G. Opelz, V. Daniel, and C. Naujokat. 2009. Salinomycin induces apoptosis and overcomes apoptosis resistance in human cancer cells. Biochem. Biophys. Res. Commun. 390:743-749.
24. Ketola, K., P. Vainio, V. Fey, O. Kallioniemi, and K. Iljin. 2010. Monensin is a potent inducer of oxidative stress and inhibitor of androgen signaling leading to apoptosis in prostate cancer cells. Mol. Cancer Ther. 9:3175-3185.

25. van, A. R. and R. Nusse. 2009. Towards an integrated view of Wnt signaling in development. Development 136:3205-3214.
26. Najdi, R., R. F. Holcombe, and M. L. Waterman. 2011. Wnt signaling and colon carcinogenesis: beyond APC. J. Carcinog. 10:5.
27. Niehrs, C. and J. Shen. 2010. Regulation of Lrp6 phosphorylation. Cell Mol. Life Sci. 67:2551-2562.
28. Kohn, A. D. and R. T. Moon. 2005. Wnt and calcium signaling: beta-catenin-independent pathways. Cell Calcium 38:439-446.
29. Ketola, K., M. Hilvo, T. Hyotylainen, A. Vuoristo, A. L. Ruskeepaa, M. Oresic, O. Kallioniemi, and K. Iljin. 2012. Salinomycin inhibits prostate cancer growth and migration via induction of oxidative stress. Br. J. Cancer 106:99-106.
30. Gupta, P. B., T. T. Onder, G. Jiang, K. Tao, C. Kuperwasser, R. A. Weinberg, and E. S. Lander. 2009. Identification of selective inhibitors of cancer stem cells by high-throughput screening. Cell 138:645-659.
31. Reya, T. and H. Clevers. 2005. Wnt signalling in stem cells and cancer. Nature 434:843-850.
32. Clevers, H. 2006. Wnt/beta-catenin signaling in development and disease. Cell 127:469-480.
33. Barker, N. and H. Clevers. 2000. Catenins, Wnt signaling and cancer. Bioessays 22:961-965.
34. Willert, K. and K. A. Jones. 2006. Wnt signaling: is the party in the nucleus? Genes Dev. 20:1394-1404.
35. Ghosh-Choudhury, N., A. Graham, and H. P. Ghosh. 1987. Herpes simplex virus type 2 glycoprotein biogenesis: effect of monensin on glycoprotein maturation, intracellular transport and virus infectivity. J. Gen. Virol. 68 (Pt 7):1939-1949.
36. Johnson, D. C. and P. G. Spear. 1982. Monensin inhibits the processing of herpes simplex virus glycoproteins, their transport to the cell surface, and the egress of virions from infected cells. J. Virol. 43:1102-1112.
37. Kaiser, C. J. and K. Radsak. 1987. Inhibition by monensin of human cytomegalovirus DNA replication. Arch. Virol. 94:229-245.
38. Lopez-Iglesias, C. and F. Puvion-Dutilleul. 1988. Effects of tunicamycin and monensin on the distribution of highly phosphorylated proteins in cells infected with herpes simplex virus type 1. J. Ultrastruct. Mol. Struct. Res. 101:173-184.
39. Angelova, M., K. Zwezdaryk, M. Ferris, B. Shan, C. A. Morris, and D. E. Sullivan. 2012. Human Cytomegalovirus Infection Dysregulates the Canonical Wnt/beta-catenin Signaling Pathway. PLoS. Pathog. 8:e1002959.
40. Bongers, G., D. Maussang, L. R. Muniz, V. M. Noriega, A. Fraile-Ramos, N. Barker, F. Marchesi, N. Thirunarayanan, H. F. Vischer, L. Qin, L. Mayer, N. Harpaz, R. Leurs, G. C. Furtado, H. Clevers, D. Tortorella, M. J. Smit, and S. A. Lira. 2010. The cytomegalovirus-encoded chemokine receptor US28 promotes intestinal neoplasia in transgenic mice. J. Clin. Invest 120:3969-3978.
41. Cheeran, M. C., J. R. Lokensgard, and M. R. Schleiss. 2009. Neuropathogenesis of congenital cytomegalovirus infection: disease mechanisms and prospects for intervention. Clin. Microbiol. Rev. 22:99-126.
42. Zhou, Y. F., F. Fang, Y. S. Dong, H. Zhou, H. Zhen, J. Liu, and G. Li. 2006. [Inhibitory effect of murine cytomegalovirus infection on neural stem cells' differentiation and its mechanisms]. Zhonghua Er. Ke. Za Zhi. 44:505-508.

I claim:

1. A method for treating human cytomegalovirus (HCMV) in a patient in need thereof comprising administering an effective amount of salinomycin.

2. A method for treating herpes simplex virus (HSV) in a patient in need thereof comprising administering an effective amount of salinomycin.

* * * * *